(12) United States Patent
Feine

(10) Patent No.: US 6,893,261 B1
(45) Date of Patent: May 17, 2005

(54) MINIATURE ULTRASONIC FOOTSWITCH GENERATOR FOR DENTAL SCALING AND METHOD

(76) Inventor: James Feine, P.O. Box 2009, Bellaire, TX (US) 77402-2009

(*) Notice: Subject to any disclaimer, the term of this patent is extended or adjusted under 35 U.S.C. 154(b) by 282 days.

(21) Appl. No.: 10/064,915

(22) Filed: Aug. 28, 2002

Related U.S. Application Data

(60) Provisional application No. 60/316,166, filed on Aug. 30, 2001, provisional application No. 60/315,681, filed on Aug. 29, 2001.

(51) Int. Cl.[7] .................................. A61C 1/02
(52) U.S. Cl. ........................ 433/101; 433/119
(58) Field of Search .................... 433/101, 86, 119; 251/295; 200/52 R, 61.58 R, 86.5

(56) References Cited

U.S. PATENT DOCUMENTS

| | | | | |
|---|---|---|---|---|
| 3,213,537 A | * | 10/1965 | Balamuth et al. | 433/98 |
| 3,924,335 A | * | 12/1975 | Balamuth et al. | 433/119 |
| 4,523,911 A | * | 6/1985 | Braetsch et al. | 433/101 |
| 4,634,420 A | * | 1/1987 | Spinosa et al. | 604/22 |
| 5,419,703 A | * | 5/1995 | Warrin et al. | 433/216 |
| 6,514,077 B1 | * | 2/2003 | Wilk | 433/216 |

* cited by examiner

*Primary Examiner*—Todd E. Manahan
(74) *Attorney, Agent, or Firm*—Daniel N. Lundeen; Lundeen & Dickinson, L.L.P.

(57) ABSTRACT

The present invention relates to a footswitch which contains all operating elements of an ultrasonic dental scaling system. The footswitch incorporates the circuitry for controlling the frequency of the dental scaling tip and can also provide water and light which is fed to a remote head located either on the dentist or hygienist or on the dental chair adjacent the patient, thereby eliminating the need for a control unit on the counter top in the treatment room. The consolidation of the entirety of the control circuitry in the footswitch eliminates messy cable tangles and because it services a remote head located adjacent the patient allows the handpiece control cable to be shortened, thus lightening the strain on the technician and permitting easier and more efficient dental scaling to be accomplished.

17 Claims, 3 Drawing Sheets

MINIATURE ULTRASONIC FOOTSWITCH GENERATOR FOR DENTAL SCALING AND METHOD

CROSS REFERENCE TO RELATED APPLICATIONS

The following applications claims the benefit of priority from U.S. Provisional Application, assigned Ser. No. 60/315,681 filed Aug. 29, 2001, and from U.S. Provisional Application, assigned Ser. No. 60/316,166, filed Aug. 30, 2001.

BACKGROUND OF INVENTION

The present invention relates to a dental scaling tool control device; specifically to a miniaturized ultrasonic dental scaling generator and control circuit providing lightweight and readily accessible controls in a footswitch which can be adjusted without reaching out to the counter where such controls are normally housed.

Prior control devices for dental scalers have been generally housed in consoles located on tables or countertops adjacent the treatment chair. All power and frequency controls were typically located on the face of the control device and required the technician who wished to adjust the power to the ultrasonic dental scaler to divert his or her attention from the patient to the console. Very often this required moving across the treatment room to modify the settings before returning to the patient in the treatment chair. So far as known to applicant, no prior art device provided all circuitry and power supply located in a convenient footswitch adjacent the treatment chair, with a remote head adjacent the patient to adjust the water flow and the frequency when a manually tuned dental scaler was in use.

By locating all circuitry necessary to control the ultrasonic dental scaler into the footswitch (including a power control), the cable bundle to the chair is shortened, thus reducing the clutter in and around the dental chair. Also, the shortening of the dental scaler handpiece control cable bundle because of the proximity of the remote head to the patient lightens the handpiece and offers less resistance to its movement, thus improving the ability of the dentist or hygienist to be able to move the handpiece to clean the patient's teeth and gums. Since the footswitch can also provide a light source for a fiber optic connection, the remote head of the present invention also provides a light system which can supply light to either the handpiece or to the dentist's or hygienist's headlight unit or lighted hand mirror, if so desired.

SUMMARY OF INVENTION

The present invention is a miniaturized ultrasonic dental scaler control device comprising a footswitch connectable to electrical service and water service which generates regulated ultrasonic power to drive either a magnetostrictive stack or a piezoelectric crystal in a handpiece to permit the removal of plaque and calculus from teeth. The control device is connected with a cable bundle to a remote control device which can be worn on the belt of the technician providing the scaling service; or, alternatively, attached to the chair adjacent the patient's head or some other location proximal to the patient. In manually adjusted systems, this remote control device can contain a needle valve, or miniature water regulator, to adjust the flow of water through the scaling tip. The footswitch enables the operator to turn on and off the ultrasonic circuitry, and also control the power as required during the cleaning process. In an automatically tuned scaling tip system or a system utilizing a piezoelectric crystal, the remote control device may be limited to adjusting the flow of water to the tip. Additionally, the miniaturized system can provide a source of light which is delivered to the tip through a fiber optic or other light conveyance media from the footswitch to the handpiece.

A footswitch for a dental scaling tip of one embodiment of this invention includes a cable for connecting an electrical power supply; a hose for connecting to a water supply; a sealed footswitch housing providing a pivoting member operable by foot to engage and disengage a power switch in said footswitch housing and a potentiometer for regulating the current through the potentiometer relative to the movement of the footswitch; a hydraulic solenoid energized by the power switch to open a valve for the movement of water through the footswitch housing to the dental scaling tip; input conduits connecting said footswitch housing to said electrical power supply and water supply; a circuit energized by the footswitch power supply to drive an oscillator for providing power in a dental scaling handpiece to a magnetostrictive stack for converting electrical energy to mechanical energy; and, a conductor bundle for transmitting electrical energy and water to a remote head, said remote head providing means for connection of a handpiece in a standard dental scaler to said footswitch power supply and for the adjustment of water flow to said dental scaling handpiece. The remote head can also provide means for adjusting the frequency of the oscillator which drives the ultrasonic dental scaler. Additionally, the footswitch housing can also provide a light source which is energized by the power switch.

This footswitch is counterless, i.e. it does not need any countertop space for the control unit, and can be used for performing dental scaling by connecting the footswitch housing to a power supply; connecting the footswitch housing to a water supply; connecting the remote head adjacent the patient to a handpiece control cable; depressing the footswitch to energize the circuit and engage the hydraulic solenoid; engaging a dental scaler and moving the footswitch to clean the teeth of a patient.

In another embodiment, a counterless ultrasonic dental scaler system features an integral housing unit for placement on the floor adjacent a dental chair; a pivoting foot platform mounted on the housing unit operatively associated with a microswitch and a potentiometer disposed within the housing unit; a hydraulic solenoid disposed in the housing unit and operatively coupled to the microswitch for opening and closing a valve in the housing unit to selectively start and stop a water supply stream; a circuit disposed in the housing unit selectively energized and de-energized by the microswitch to drive an oscillator for providing power to a magnetostrictive stack, or alternatively, a piezoelectric crystal in a dental scaler handpiece remote from the housing unit at or near a resonant frequency for ultrasonically vibrating a scaling tip coupled to the stack (or crystal) via a velocity transducer; electrical and water input conductors connected to the housing unit; a main cable connecting the dental scaler handpiece to the housing unit, the cable comprising an electrical conductor for transmitting the power to the stack and a water conductor for supplying water to the handpiece. The counterless ultrasonic dental scaler system further features a control unit attached to the main cable intermediate the housing unit and the handpiece and a fastener operatively associated with the control unit for releasably mounting the control unit to a structure within reach of a dental practitioner operating the system, the control unit including a valve in the water conductor for controlling the water supply stream. The counterless ultrasonic dental scaler system can either provide the circuit which includes an automatic tuning feature leaving the control unit is free of additional controls other than the valve or it may provide a manual tune feature comprising a frequency adjustment input device associated with the controller and operatively coupled to the circuit via the main cable. The control unit may be mounted on the dental chair or on the person of the technician providing the dental scaling service. Finally, the system may further provide a light supply source in the housing unit energized by the microswitch and operatively coupled via the main cable to a light emitter disposed adjacent the handpiece for illumination of the tip. The light supply source can be fiberoptically coupled to the light emitter or it may provide other technologies for light transmission.

DETAILED DESCRIPTION

Figure 1:
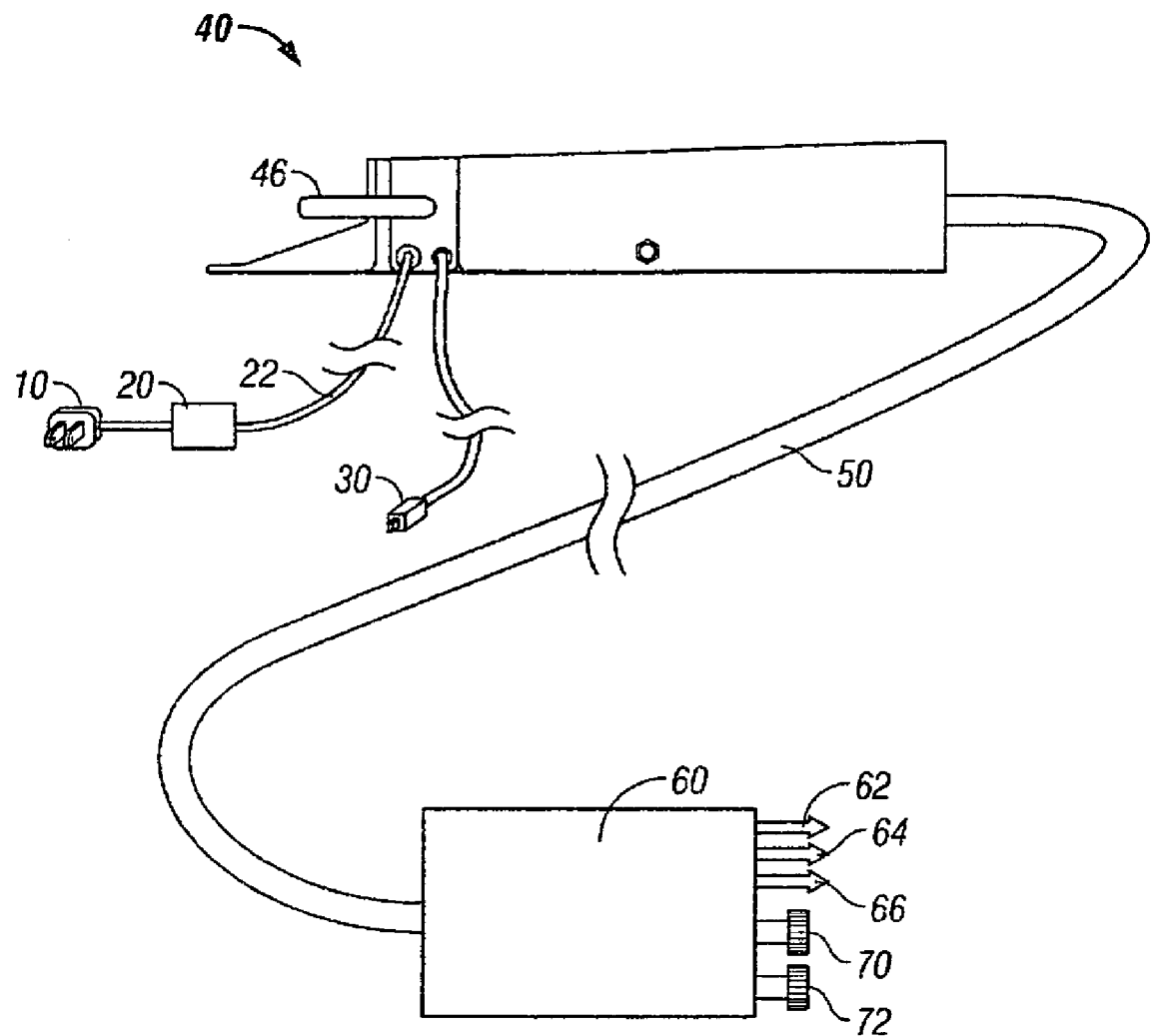
FIG. 1 is a schematic view of the components of the present invention.

Electrical power and water are connected to the power level control footswitch, which also contains the circuitry to drive the oscillator to provide the power to the magnetostrictive stack in a manner well known in this art. FIG. 1 is a schematic view of the components of the present system. Electrical connection is made to a standard AC outlet 10. A transformer 20, or alternatively a switched power supply unit, for the footswitch 40 is built into the inlet power cord 22. Alternatively, the power supply unit and circuit could be incorporated into the footswitch container, all in a manner well known in the industry. The footswitch 40 is additionally connected to a water source 30.

Figure 2:
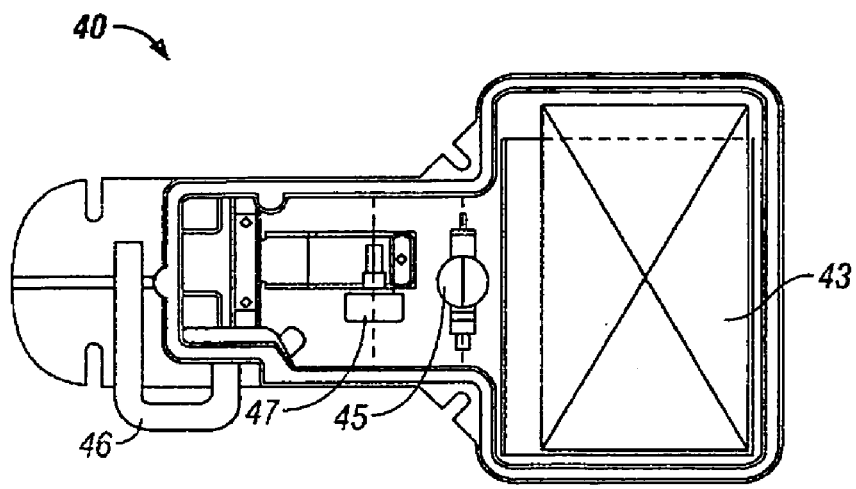
FIG. 2 is a schematic top view of the footswitch of the present invention.
Figure 3:
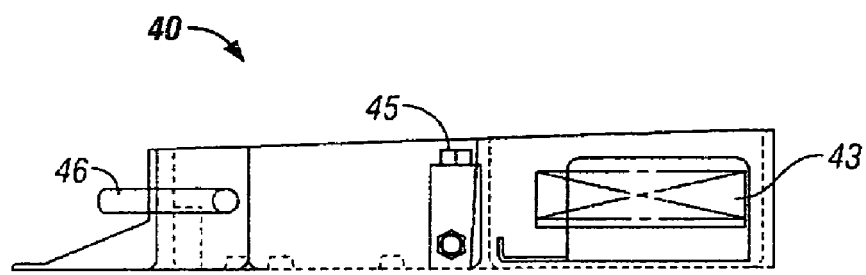
FIG. 3 is a schematic side view of the footswitch of the present invention.
Figure 3A:
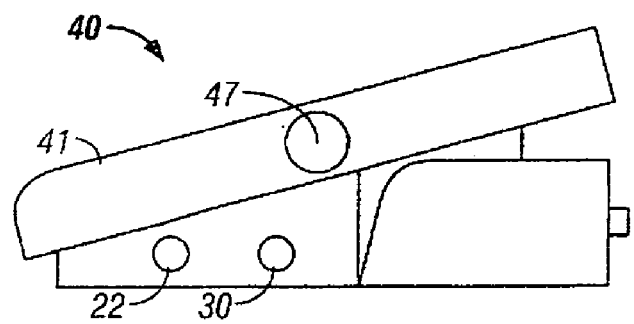
FIG. 3A is a schematic side view of another embodiment of the footswitch of the present invention.

The footswitch 40 provides a microswitch that is depressed to turn the power on. Thereafter the amount of current delivered to the handpiece is regulated by the movement of the potentiometer connected to the pivot bar 46 (or alternatively, in the pivoting upper surface 41 of footswitch 40 as more clearly shown in FIG. 3a). Footswitch 40 is made from heavy gauge aluminum which is both rugged and capable of absorbing and dissipating all heat generated by the circuit board. For additional cooling, the water flow to the tip may be circulated around the circuitry to remove excess heat from the footswitch. In addition to the potentiometer which is moved by the movement of the dentist's or hygienist's foot on the pivot bar 46 of the footswitch 40 (as more fully shown in FIGS. 1, 2 and 3) or on the top surface 41 (as more clearly shown in FIG. 3a) of the footswitch 40, footswitch 40 also contains a hydraulic solenoid 45 which is activated by the micro power switch to permit water to flow to the handpiece. The oscillator circuitry 43 of the present invention has been reduced in size and incorporated in the footswitch 40, as more fully illustrated in FIG. 2. This consolidation of elements of the standard dental scaling system eliminates the control housing from the counter around the treatment areas found in all prior art devices. The circuit board 43 of the present invention is approximately five inches square and no more than one inch high thereby permitting the consolidation of this board with the footswitch. The inner portion of the footswitch is sealed to dust, water and other contaminants in a manner well known in the art and provides a potentiometer 47 connected to the pivot bar 46 of one embodiment (FIGS. 1–3) or to the upper surface 41 of the footswitch 40 (FIG. 3a). The footswitch 40 also contains an electrical actuated hydraulic solenoid 45 which opens upon being energized by the microswitch (not shown) depressed by moving the pivot bar 46 or upper surface 41 all the way to the maximum power position on the footswitch 40. The pivot bar 46 and the upper surface 41 are spring-loaded to return the power level to the lowest level after startup.

The footswitch 40 can also provide a light source, such as argon lamp, to provide a source of light to a fiber optic light guide or other light conveyance media disposed in the cable bundle 50 connected from the footswitch 40 to the remote head 60 of the present invention. The remote head 60 is designed to accept the cable bundle 50 and can be attached either to the treatment chair in the manner shown in FIG. 4 or it may be worn on the belt of the dentist or hygienist for ready accessibility.

The water conduit 30 supplied to the footswitch 40 passes through a cooling block inside the ultrasonic generator and removes excess heat produced by the circuitry. This prewarms the inlet water to the handpiece providing a more gentle lavage action for the patient. Heat detectors can be built into the handpiece and ultrasonic generator to shut off the unit if it heats beyond a preset heat limit to avoid damage to the unit and harm to the patient.

For a manually tuned dental scaling system, the remote head 60 can provide either a needle valve adjustment 70, or a miniature water regulator, for the water flow to the dental scaling tip as well as a potentiometer 72 for adjusting the frequency of the power delivered to the dental scaling tip. The remote head 60 provides a connection means for the handpiece cable which provides the water 62, light 64 and power 66 to the shortened handpiece cable 81, connected to a ultrasonic dental scaler 80, more clearly shown in FIG. 4. As may be readily appreciated, the remote head 60 would not need a potentiometer for adjusting an automatically tuned magnetostrictive dental scaler 80 and this additional control feature may be eliminated from the remote head 60, if desired.

Figure 4:
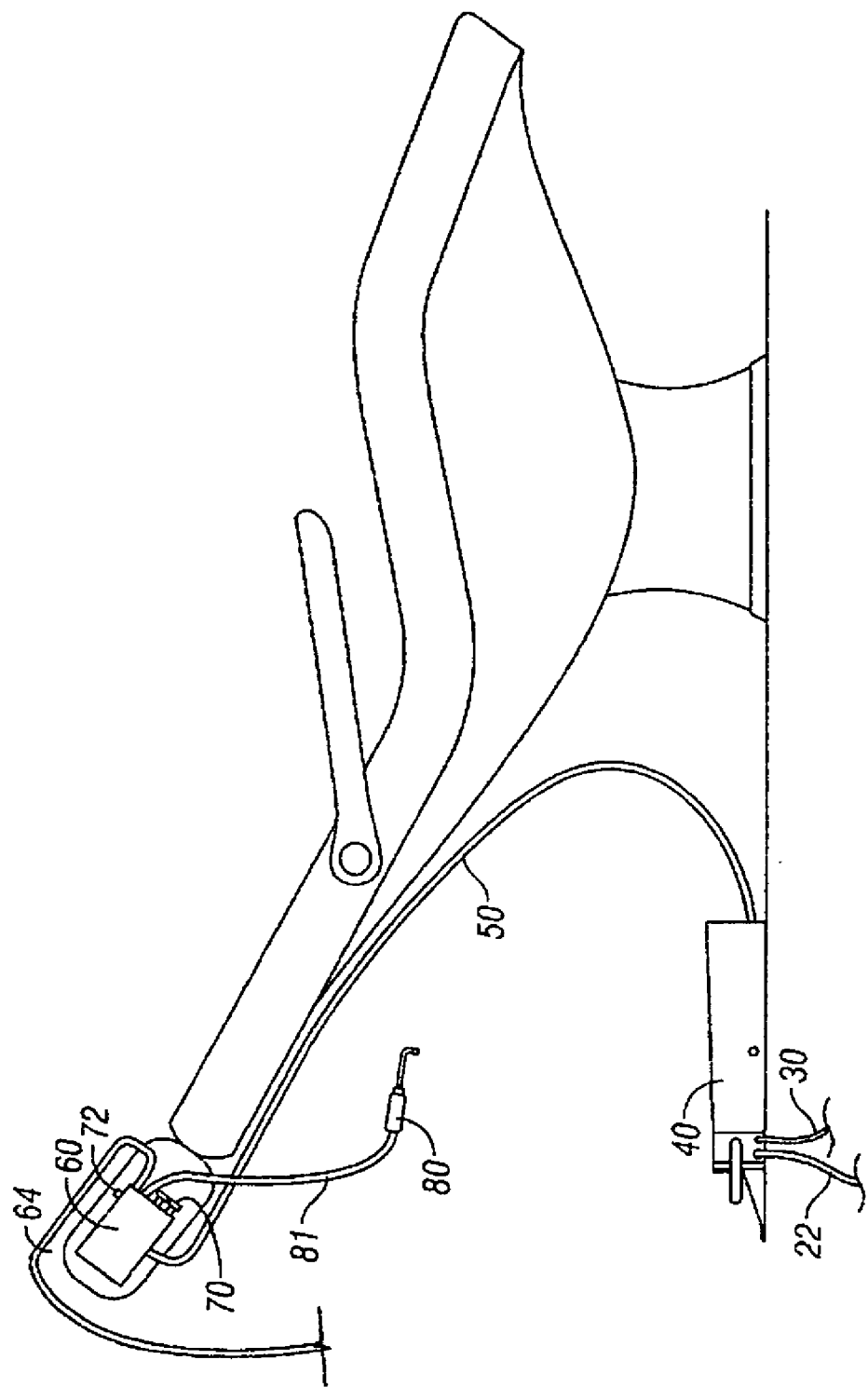
FIG. 4 is a schematic view of the footswitch, with the remote head mounted on the dental chair.

FIG. 4 shows another configuration of the present invention with the remote head 60 attached to the headrest of the reclining dental chair. This attachment can be accomplished by two-sided Velcro™ tape which can thereafter hold the remote head on the normal pad commonly found on most dental chairs, or it may be attached in any of a number of ways in a manner well known to those in the dental supply industry. Since the remote head 60 is adjacent the patient, rapid adjustments may be made to the water 62 by turning needle valve 70 (or alternatively, a water regulator) and frequency 66 by turning potentiometer 72, if the system is a manually tuned system, without moving away from the patient receiving treatment. In an automatically tuned system, as previously described, the sole adjustment is made to the water supply 62, as well as power to the ultrasonic scaling tip based upon the position of the footswitch pivot bar 46 or footswitch top cover 41. The optional fiber optic cable outlet 64 from the remote head 60 can be attached to a light guide in the handpiece 80 (not shown) or to a headlight unit worn by the dentist or hygienist (also not shown), or other lighted dental tools, such as a hand scraper, or a lighted mirror as desired.

As may be readily appreciated by those having ordinary skill in this art, the footswitch system of the present invention may be readily adapted for use with another transducer system: a piezoelectric dental scaler system. In such systems, the frequency of the circuit matches the frequency of the crystal which thereafter oscillates at a given frequency driving the scaling tip. Accordingly, the handpiece of a piezoelectric dental scaler could be attached to the cable bundle 50 coming into the remote head 60 of the present invention. Since the piezoelectric crystal resonant frequency is fixed, no frequency adjustment need be provided on the remote head 60 of the present invention.

As may be readily appreciated by those skilled in this art, the present footswitch system can accommodate both manually or automatically tuned magnetostrictive stack systems and permit the use of multiple frequencies in the handpiece. Additional features can include the ability to run water through the system without turning on the ultrasonic generator. This may be accomplished by depressing the footswitch to activate the micro on/off switch but refraining from moving the pivot bar 46 or footpedal 41 to change the potentiometer. If the alternative light source is involved, the light can also be activated without engaging the ultrasonic generator. This permits the operator to inspect and lavage the mouth and gums of the patient without the risk of inadvertently touching the patient with an energized scaling tip.

The foregoing description of the invention is illustrative and explanatory thereof. Various changes in the materials, apparatus, and particular parts employed will occur to those skilled in the art. It is intended that all such variations within the scope and spirit of the appended claims be embraced thereby.

What is claimed is:

1. A footswitch for a dental scaler, comprising:
   a sealed footswitch housing, the footswitch housing including a power switch disposed within the housing, a pivoting member operable by a foot to engage and disengage a power switch in the footswitch housing, a circuit energized by the power switch to drive an oscillator for providing power to an ultrasonic transducer in a dental scaler for converting electrical energy to mechanical energy, and a potentiometer for regulating the power to an ultrasonic transducer relative to the movement of the footswitch; and a hydraulic solenoid energized by the power switch for opening a valve disposed in the housing for causing the movement of water through the footswitch housing to the dental scaler;
   a cable for connecting an electrical power supply to the housing;
   a hose for connecting to a water supply to the housing;
   a remote head for providing an electrical and a fluid connection to a handpiece of the dental scaler and a valve disposed in the head for the adjustment of water flow to the handpiece; and,
   a conductor bundle for providing an electrical and a fluid connection between the footswitch housing and the head.

2. The footswitch of claim 1 wherein the ultrasonic transducer is a magnetostrictive stack and velocity transducer.

3. The footswitch of claim 1 wherein the ultrasonic transducer is a piezoelectric crystal and velocity transducer.

4. The footswitch of claim 1 wherein the remote head on said conductor bundle includes an input device for changing the frequency of the oscillator in said footswitch housing.

5. The footswitch of claim 1 further comprising a light source.

6. The footswitch of claim 5 wherein the light source is energized by the power switch.

7. A method for performing dental scaling comprising:
   connecting the footswitch housing of claim 1 to a power supply;
   connecting the footswitch housing of claim 1 to a water supply;
   connecting the remote head of claim 1 adjacent a patient to a handpiece control cable;
   depressing the footswitch to energize the circuit and engage the hydraulic solenoid;
   engaging a dental scaler and moving the footswitch to clean the teeth of a patient.

8. A counterless ultrasonic dental scaler system, comprising:
   an integral housing unit for placement on the floor adjacent a dental chair;
   a pivoting foot platform mounted on the housing unit operatively associated with a microswitch and a potentiometer disposed in the housing unit;
   a hydraulic solenoid disposed in the housing unit and operatively coupled to the microswitch for opening and closing a valve in the housing unit to selectively start and stop a water supply stream;
   a circuit disposed in the housing unit selectively energized and de-energized by the microswitch to drive an oscillator for providing power to an ultrasonic transducer in a dental scaler handpiece remote from the housing unit at or near a resonant frequency for ultrasonically vibrating a scaling tip coupled to the stack via a velocity transducer;
   electrical and water input conductors connected to the housing unit;
   a main cable connecting the dental scaler handpiece to the housing unit, the cable comprising an electrical conductor for transmitting the power to the stack and a water conductor for supplying water to the handpiece.

9. The counterless ultrasonic dental scaler of claim 8 wherein the ultrasonic transducer is a magnetostrictive stack coupled to a velocity transducer.

10. The counterless ultrasonic dental scaler of claim 8 wherein the ultrasonic transducer is a piezoelectric crystal coupled to a velocity transducer.

11. The counterless ultrasonic dental scaler of claim 8 further comprising a light supply source in the housing unit energized by the microswitch and operatively coupled via the main cable to a light emitter disposed adjacent the handpiece for illumination of the tip.

12. The counterless ultrasonic dental scaler system of claim 8 further comprising a control unit attached to the main cable intermediate the housing unit and the handpiece and a fastener operatively associated with the control unit for releasably mounting the control unit to a structure within reach of a dental practitioner operating the system, the control unit including a valve in the water conductor for controlling the water supply stream.

13. The counterless ultrasonic dental scaler system of claim 9 wherein the circuit includes an automatic tuning feature and the control unit is free of additional controls other than the valve.

14. The counterless ultrasonic dental scaler of claim 9 further comprising a manual tune feature comprising a frequency adjustment input device associated with the controller and operatively coupled to the circuit via the main cable.

15. The counterless ultrasonic dental scaler of claim 9 wherein the mounting structure is the dental chair.

16. The counterless ultrasonic dental scaler of claim 9 wherein the mounting structure is the dental practitioner.

17. The counterless ultrasonic dental scaler of claim 11 wherein the light supply source is fiberoptically coupled to the light emitter.

* * * * *